Dec. 20, 1932. N. GRILLO Plant Pat. 49
HYBRID TEA ROSE
Filed April 28, 1932
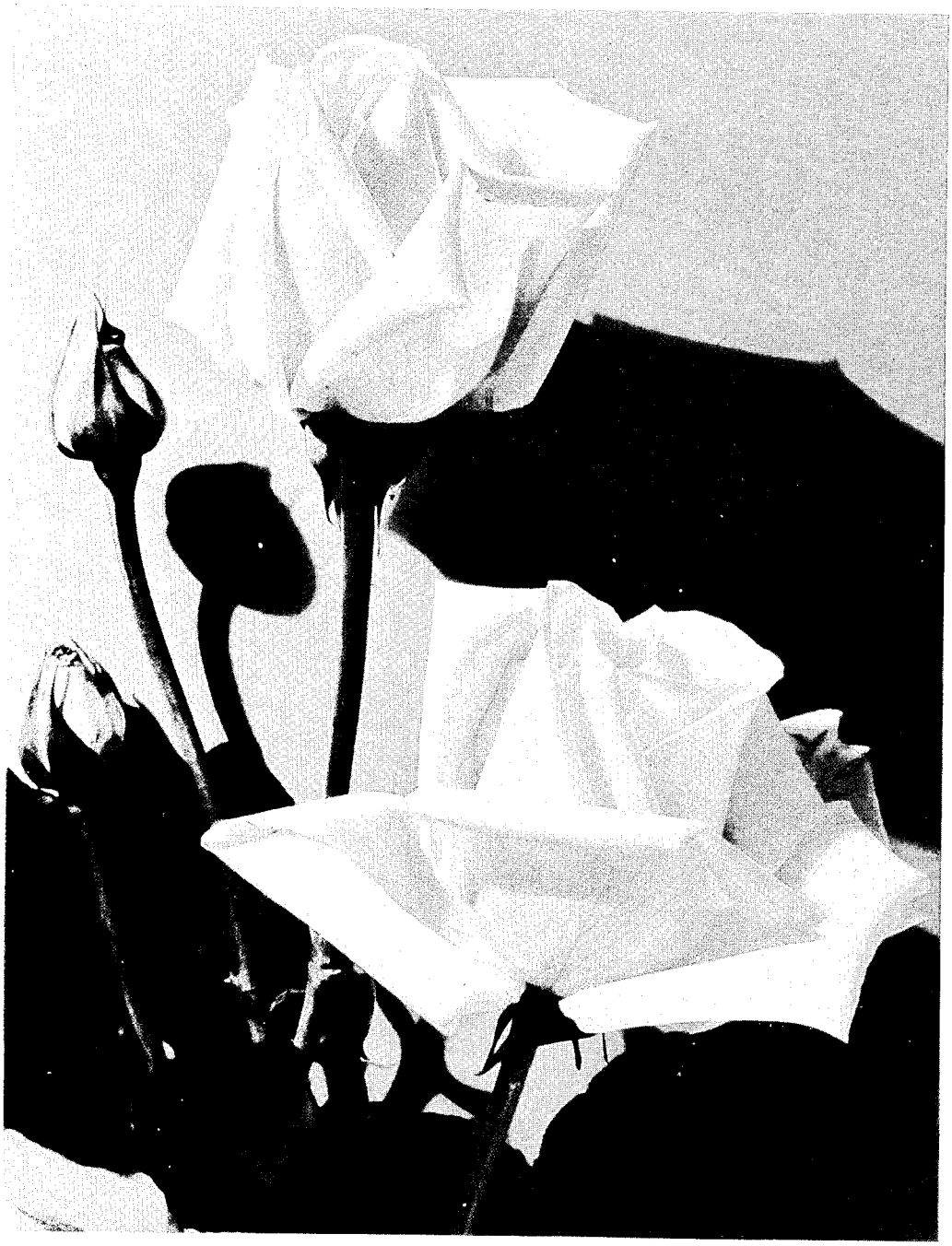
Inventor
Nicholas Grillo
By Orville M. Kile
Plant Patent Agent Patented Dec. 20, 1932

Plant Pat. 49

UNITED STATES PATENT OFFICE

NICHOLAS GRILLO, OF MILLDALE, CONNECTICUT

HYBRID TEA ROSE

Application filed April 28, 1932. Serial No. 608,091.

My new variety of rose is of a beautiful white color, at times slightly suffused with pink, has a desirable (pointed) form and size, and superior growing qualities.

I first discovered this new variety in the spring of 1928. It originated as a sport of the rose Grillodale, which in turn is a sport of Madam Butterfly. Following the discovery of this sport, I carefully observed and tested it and have since reproduced from cuttings a considerable number of plants which are in all important respects identical with the parent plant, but the variety has not yet been offered for sale.

The accompanying illustrations show in full color two partly opened flowers and two tightly rolled immature buds, as well as leaves and stems.

The following is a detailed description of this rose, but it must be understood that there may be some variation as between particular specimens.

A bush or upright Hybrid Tea Rose of medium height, vigorous of growth, having much foliage, resistant to disease, and being a profuse bloomer.

*Stems.*—Medium stout to stout, with few thorns, most stems having but one or two medium-sized pink thorns pointing downward. Stem is zig-zag rather than straight except for the first 3 to 3½ inches below the flower (the peduncle) which is straight or slightly curved. The stem carries an unusual number of leaf branches, set only 1½ to 2 inches apart.

Leaves are large and heavy, usually measuring 2½ to 3 inches in length and proportionately broad, arranged five to a leaf branch, except in the case of the immature leaf branches immediately below the peduncle. The petioles are notably pinkish on upper surfaces. An occasional leaf branch bears a single small spine about midway of the central stem. Leaves are of rich green color, not glossy, and the serrations on the edges of the leaves are small. The crinkled form of the edges of the leaves is notable.

Stipules are medium wide, ordinarily one-half to three-quarters inch long.

*Hips.*—Medium width and moderately tapering.

*Buds.*—When opening are 1½ inches long, excluding hips.

*Sepals.*—5 in number, notably short and wide at base with decided tendency to curl back tightly as soon as the bud has opened. The sepals on an average flower are 1 inch long, have a sharply tapered point and a width of ½ inch for the basal half, heavy and non-foliaceous.

Flowers are borne singly and are 3½ to 4½ inches across when well opened. The newly opened bud with sepals turned tightly back around the hips, is pointed or conical in shape and this same shape is retained in the central portion of the flower until it has fully opened and passed its prime. The outer five or six petals each roll or curl back along two edges in such a way as to assume triangular forms with the apex of each triangle at the topmost point, thus forming a beautiful setting for the central conical portion of the flower. While the shape of this new rose is somewhat similar to that of the well known Kaiserin Auguste Viktoria, it differs materially from the latter in size, color tints, foliage, stems and growing habits.

*Petallage.*—The flower in March has but 20 to 30 petals, but these are all large petals and the peculiar raised structure of the basal portion of the center of the flower, combined with the fact that the central petals remain rolled together at the top, gives the effect of a rose having a much larger number of petals. This exceptionally high basal structure referred to is caused by the extraordinary number of pistils and stamens with accompanying fibrous material. The pistils are white with pinkish tops and the stamens are mounted by large yellow anthers. To all outward appearances the flower might be expected to have ten or a dozen more petals than are shown by actual count.

*Color.*—The petals have a slight lemon tint around the base but none is visible to the casual observer anywhere in the flower until the outer petals begin to turn back and show their inner bases. While the artist may see a slight suffusion of lemon at points, the effect to the casual observer is pure white except on those specimens which show the characteristic slight pink suffusion on the edges of a few petals and at the center. This slight pink color is not found on all roses of this variety, sometimes only on a part of the blossoms growing on a given bush. In most cases the tint is considerably less pronounced than in the specimens shown in the illustrations.

*Reproduction.*—A further valuable quality is found in the fact that this variety reproduces readily, producing practically no "blind" wood.

What I claim as new is:

The hybrid tea rose herein shown and described, characterized particularly by its large white flowers having conical or pointed centers, often slightly suffused with pink.

In testimony whereof I affix my signature.

NICHOLAS GRILLO.